United States Patent [19]

Light et al.

[11] 4,084,009

[45] Apr. 11, 1978

[54] FLAVORING WITH A HYDROXY CYCLOHEXENONE DERIVATIVE

[75] Inventors: Kenneth K. Light, Long Branch; Bette M. Spencer, Ocean Grove; Joaquin F. Vinals, Red Bank, all of N.J.; Jacob Kiwala, Brooklyn, N.Y.; Manfred Hugo Vock, Locust, N.J.; Edward J. Shuster, Brooklyn, N.Y.

[73] Assignee: International Flavors & Fragrances Inc., New York, N.Y.

[21] Appl. No.: 774,059

[22] Filed: Mar. 3, 1977

[51] Int. Cl.² ............................................. A23L 1/226
[52] U.S. Cl. .................................. 426/538; 252/522; 260/586 R; 131/17 R
[58] Field of Search ...................... 260/586 R; 426/538

[56] References Cited

U.S. PATENT DOCUMENTS

| | | | |
|---|---|---|---|
| 3,923,898 | 12/1975 | Schulte-Elte | 426/538 X |
| 3,927,107 | 12/1975 | Schulte-Elte | 426/538 X |
| 3,957,877 | 5/1976 | Schulte-Elte | 260/586 R |
| 3,962,148 | 6/1976 | Hochstetler | 260/586 R X |
| 3,989,857 | 11/1976 | Demole | 426/538 X |
| 4,029,106 | 6/1977 | Demole | 426/538 X |

Primary Examiner—Joseph M. Golian
Attorney, Agent, or Firm—Arthur L. Liberman; Franklin D. Wolffe

[57] ABSTRACT

Processes and compositions are described for the use in foodstuff, chewing gum, toothpaste and medicinal product flavor and aroma, tobacco flavor and aroma, perfume and perfumed article aroma augmenting, enhancing and imparting compositions and as foodstuff, chewing gum, toothpaste, medicinal product, tobacco, perfume and perfumed article aroma imparting materials of hydroxy cyclohexenone derivatives having the generic formula:

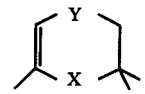

wherein one of X and Y is a keto moiety having the structure:

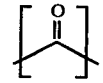

and the other of X and Y is a carbinol moiety having the structure:

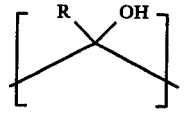

and wherein R is $C_1$-$C_5$ alkyl.

2 Claims, 6 Drawing Figures

NMR SPECTRUM ACCORDING TO EXAMPLE II

SOLVENT: $CDCl_3$
SWEEP WIDTH: 1000 Hz.

IR SPECTRUM ACCORDING TO EXAMPLE II

IR SPECTRUM ACCORDING TO EXAMPLE IV

FLAVORING WITH A HYDROXY CYCLOHEXENONE DERIVATIVE

BACKGROUND OF THE INVENTION

The present invention relates to hydroxy cyclohexenone derivatives having the generic formula:

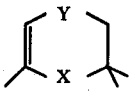

wherein one of X and Y is a keto moiety having the structure:

and the other of X and Y is a carbinol moiety having the structure:

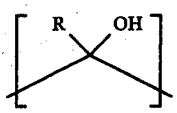

and wherein R is $C_1$–$C_5$ alkyl produced by the processes of our invention and novel compositions using one or more of such hydroxy cyclohexenone derivatives to augment or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply and to provide more uniform properties in the finished product.

Citrus/labdanum, sweet and woody aromas with sweet, woody, earthy and labdanum flavor characteristics are particularly desirable for many uses in foodstuff flavorings, chewing gum flavors, toothpaste flavors and medicinal product flavors.

Green, minty, herbaceous, strong fruity aromas with earthy, mossy notes are desirable in several types of perfume compositions, perfumed articles and colognes.

Sweet, tobacco-like, floral and green aromas prior to smoking and bright tobacco-like notes on smoking are particularly desirable in tobaccos and tobacco flavoring materials.

The compound having the structure:

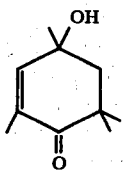

is disclosed by Maheshwari, et al in Canadian Journal of Chemistry, Vol. 48, 1970, pages 3265–3268; however, the organoleptic uses of such compound are not set forth.

A compound having the common name "Blumenol-C" having the structure:

is disclosed as having been isolated from Burley tobacco flavor by Demole and Enggist at page 2088, Helv.-Chim.Acta., Vol. 57, Fasc. 7 (1974) and also by Aasen, et al, Acta.Chem.Scandinavia, B 28 (1974), pages 285–8.

Also disclosed are U.S. Pat. Nos. 3,793,375 and 3,839,421 as being useful as plant growth regulators are compounds having the structures:

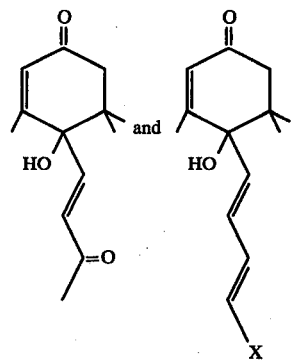

However, none of the compounds of the prior art have been heretofore determined to have the organoleptic properties that the compounds of the instant invention have.

THE INVENTION

Figure 1:
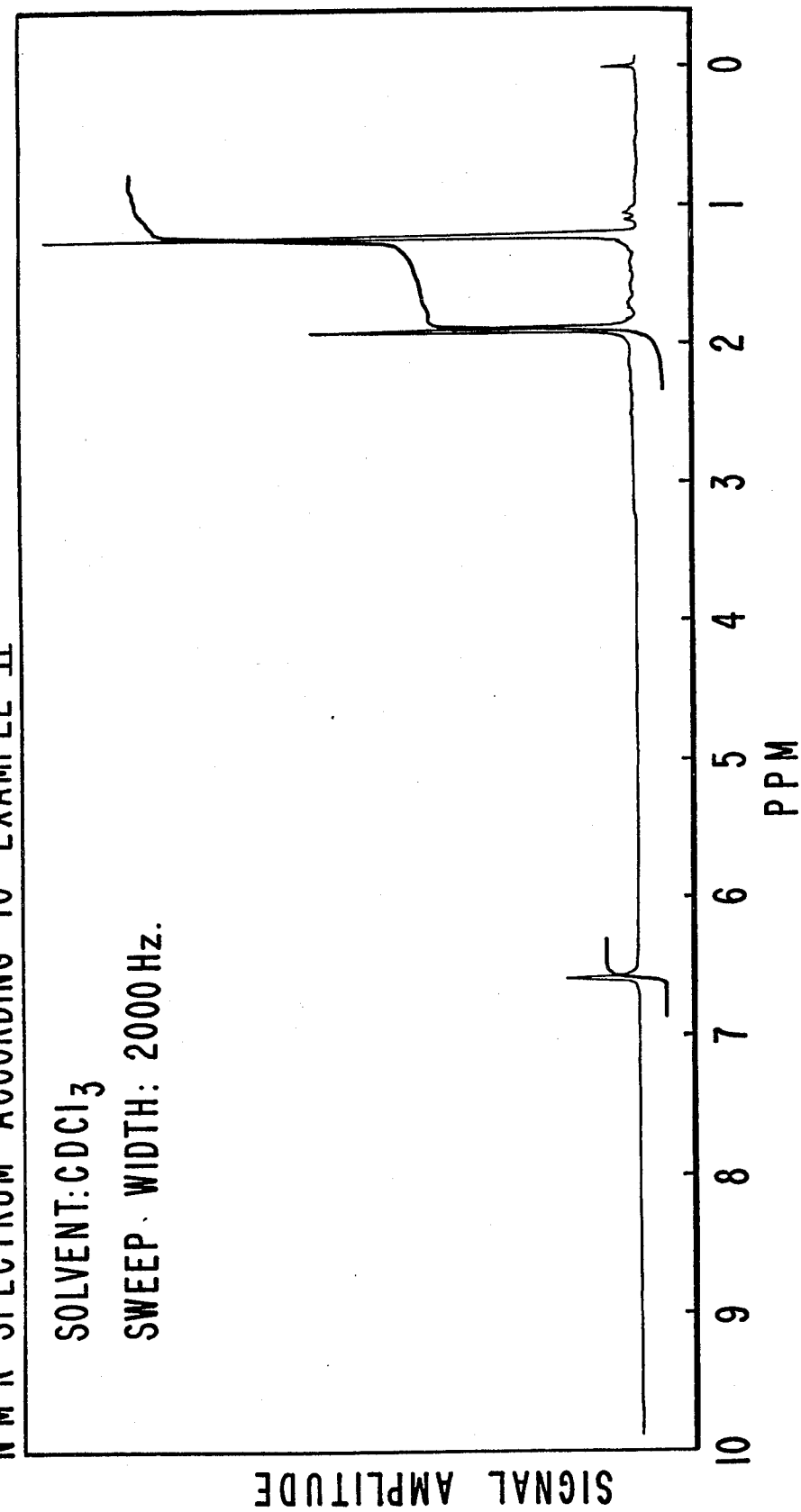
FIG. 1 represents the NMR spectrum for one of the compounds produced according to Example II, namely, 4-hydroxy-2,4,6,6-tetramethylcyclohex-2-en-1-one and 2,4,4,6-tetramethylcyclohexa-2,5-diene-1-one.

It has now been discovered that novel solid and liquid foodstuff, chewing gum, medicinal product, toothpaste and tobacco compositions and flavoring compositions therefor having citrus/labdanum, sweet and woody aromas with sweet, woody, earthy and labdanum flavor characteristics; novel perfume compositions, colognes and perfumed articles having green, minty, herbaceous, strong fruity aromas with earthy and mossy notes; and tobaccos and tobacco flavoring compositions having sweet, tobacco-like, floral and green aromas prior to smoking and bright tobacco-like notes on smoking, may be provided by the utilization of one or more hydroxy cyclohexenone derivatives having the formula:

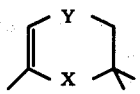

wherein one of X and Y is a keto moiety having the structure:

and the other of X and Y is a carbinol moiety having the structure:

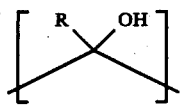

in foodstuffs, chewing gums, toothpastes, medicinal product flavors, perfumes, perfumed articles, colognes, tobaccos and tobacco flavors.

The hydroxy cyclohexenone derivatives useful as indicated supra, may be produced by one or two processes:

(i) subjecting 1,3,5,5-tetramethylcyclohexa-1,3-diene to an oxidation step comprising continuously insufflating air or oxygen through said diene at a temperature of between 15° and 30° C, while agitating said diene and irradiating said diene with ultraviolet light in the presence of an alkali metal hydroxide and Rose Bengal according to the following reaction sequence:

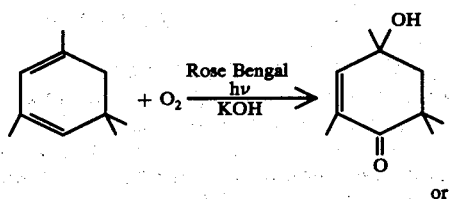

or (ii) reacting 2,7,9,9-tetramethyl-1,4-dioxaspiro[4,5]-dec-6-en-8-one with an alkyl lithium to form a lithium salt and then hydrolyzing the salt while simultaneously deketalizing the resulting compound according to the following reaction sequence:

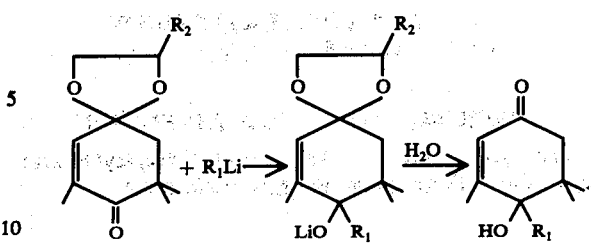

wherein $R_1$ is $C_1$–$C_4$ alkyl and $R_2$ is lower alkyl or H.

The photo-oxidation reaction is preferably carried out in an inert solvent such as methanol or a methanol-benzene mixture in the presence of a reaction sensitizer such as Rose Bengal and a base such as sodium hydroxide and potassium hydroxide. The photo-oxidation is carried out by bubbling oxygen through the reaction mass and the time of reaction as well as the rate of reaction is a function of the following variables:

1. Bubble size of oxygen;
2. Throughput of oxygen per unit of time;
3. Pressure;
4. Concentration of base in reaction mass; and
5. Concentration of UV sensitizer in reaction mass.

Higher pressures give rise to longer oxygen residence time thereby permitting shorter times of reaction and greater yields per unit time. Higher concentrations of reaction sensitizer give rise to faster reaction rates:up to sensitizer concentrations of 0.5 gm per liter and sensitizer:diene ratios 0.5:4, whereat increase in sensitizer concentration does not give rise to any material increase in reaction rate. It is preferable to carry out the photo-oxidation reaction at a temperature of between 15° and 30° C with room temperature being most convenient.

In the reaction of alkyl lithium with the compound having the structure:

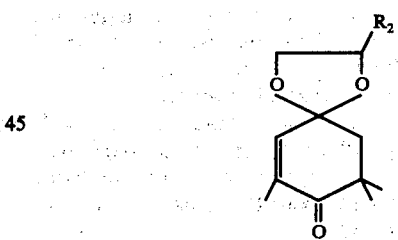

any ketal may be used in addition to the cyclic ketals exemplified above; e.g., diethyl ketals, dimethyl ketals and ethylene glycol ketals, wherein $R_2$ is H; or $R_2$ could be alkyl ($C_1$–$C_8$).

The first step of the reaction is preferably carried out in the presence of an inert solvent such as n-hexane or cyclohexane at a temperature of between 15° C and the reflux temperature of the solvent; preferably at room temperature. The alkyl lithium in inert solution is preferably added dropwise to a solution of the ketal reactant until no additional exotherm occurs.

The hydrolysis of the lithium salt moiety and the ketal moiety then takes place merely with addition of water. The temperature of the second reaction may vary from 15° C up to 70° C, but most conveniently and preferably may take place at room temperature.

The compound having the structure:

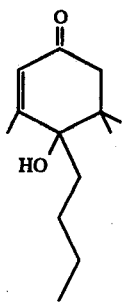

is a novel compound having unexpected, unobvious properties over the known compound of the genus of our invention having the structure:

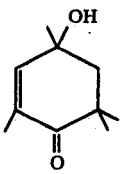

Examples and organoleptic properties of materials produced according to the aforementioned processes are as follows:

"enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the hydroxy cyclohexenone derivatives of our invention, and in addition, sweetening agents which may be sugars, including sucrose or dextrose and/or artifical sweeteners such as cyclamates or saccharin. Other optional ingredients may also be present.

Substances suitable for use herein as co-ingredients or

TABLE I

| NAME | STRUCTURE | ORGANOLEPTIC PROPERTIES | | |
|---|---|---|---|---|
| | | FLAVOR | FRAGRANCE | TOBACCO AROMA AND FLAVOR |
| 2-hydroxy-2,4,6,6-tetramethylcyclohex-2-en-1-one | OH structure | Citrus/labdanum, sweet woody aroma characteristics with sweet, woody, earthy, labdanum/citrus flavor characteristics at 10 ppm. | Minty, green, herbaceous aroma. | Sweet tobacco-like. floral, green aroma with slight cooling effect prior to smoking and bright tobacco-like aroma and taste with sweet and floral nuances in the mainstream and in the sidestream. |
| 4-butyl-4-hydroxy-3,5,5-trimethyl-2-cyclohexen-2-one | structure | Bitter chemical. | Strong fruity and earthy mossy aroma with herbaceous, green, sweet, woody, minty and slightly earthy nuances. | Sweet, hay-like, Virginia tobacco, flue-cured-like, aroma with floral and sweet hay nuances prior to and on smoking in the main and sidestreams. |

When the hydroxy cyclohexenone derivatives of our invention are used as food flavor adjuvants, the nature of the co-ingredients included with each of the said hydroxy cyclohexenone derivatives in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles broadly comprising stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxytoluene (2,6-di-tertiary-butyl-4-methylphenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like; buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta, beta-dimethylacrolein, methyl-n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, -2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten:1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethylnaphthalene, dodecane, methyldiphenyl, methylnaphthalene, myrcene, naphthalene, octadecane, tetradecane, tetramethylnaphthalene, tridecane, trimethylnaphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the hydroxy cyclohexenone derivatives of our invention by not covering or spoiling the organoleptic properties (aroma and/or taste) thereof; (ii) be non-reactive with the hydroxy cyclohexenone derivatives of our invention and (ii) be capable of providing an environment in which the hydroxy cyclohexenone derivatives can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product, toothpaste or tobacco to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the hydroxy cyclohexenone derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, tobacco per se, or flavoring composition.

The use of insufficient quantities of the hydroxy cyclohexenone derivatives will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions, toothpaste compositions and tobacco compositions, it is found that quantities of the hydroxy cyclohexenone derivatives ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein hydroxy cyclohexenone derivatives are added to the foodstuff as an integral component of a flavoring composition, it is, of course, essential that the total quantity of flavoring composition employed be sufficient to yield an effective concentration in the foodstuff product.

Food flavoring compositions prepared in accordance with the present invention preferably contain the hydroxy cyclohexenone derivatives in concentrations from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the hydroxy cyclohexenone derivatives with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the hydroxy cyclohexenone derivatives in a dry blender until the requisite degree of uniformity is achieved.

It is presently preferred to combine with the hydroxy cyclohexenone derivatives of our invention, the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methylfurfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
Damascone (1-crotonyl-2,2,6-trimethylcyclohex-1-one);
Damascenone (1-crotonyl-2,2,6-trimethylcyclohexa-1,5-diene);
Beta-cyclohomocitral (2,2,6-trimethylcyclohex1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl)-norbornadiene prepared according to Example II of U.S. Pat. No. 3,911,028, issued on Oct. 7. 1975.

The hydroxy cyclohexenone derivatives of our invention and one or more auxiliary perfume ingredients, including, for example, alcohols, aldehydes, nitriles, esters, cyclic esters and natural essential oils, may be admixed so that the combined odors of the individual components produce a pleasant and desired fragrance, particularly and preferably in herbal fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the overall sensory effect of the perfume composition will be at least the sum total of the effects of each of the ingredients. Thus, one or more hydroxy cyclohexenone derivatives can be used to alter, modify or enhance the aroma characteristics of a perfume composition, for example, by utilizing or moderating the olfactory reaction contributed by another ingredient in the composition.

The amount of hydroxy cyclohexenone derivatives of our invention which will be effective in perfume compositions as well as in perfumed articles and colognes depends on many factors, including the other ingredients, their amounts and the effects which are desired. It has been found that perfume compositions containing as little as 0.01% of a hydroxy cyclohexenone derivative(s) or even less (e.g., 0.005% can be used to impart a green, minty, herbaceous, strong fruity aroma with earthy and mossy notes to soaps, cosmetics or other products. The amount employed can range up to 70% of the fragrance components and will depend on considerations of cost, nature of the end product, the effect desired on the finished product and the particular fragrance sought.

The hydroxy cyclohexenone derivatives of our invention are useful [taken along or together with other ingredients in perfume compositions] as an olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of hydroxy cyclohexenone derivatives will suffice to impart an intense green note to herbal formulations. Generally, no more than 3% of hydroxy cyclohexenone derivatives based on the ultimate end product, is required in the perfume composition.

In addition, the perfume compositions or fragrance composition of our invention can contain a vehicle, or carrier for the hydroxy cyclohexenone derivatives. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the hydroxy cyclohexenone derivatives of our invention can be utilized to alter, modify or enhance sensory properties, particularly organoleptic properties, such as flavor(s) and/or fragrances(s) of a wide variety of consumable materials.

An additional aspect of our invention provides an organoleptically improved smoking tobacco product and additives therefor including methods of making the same which overcome problems heretofore encountered in the creation or enhancement of specific desired sweet, hay-like, Virginia tobacco-like, flue cured-like aromas with floral and sweet hay nuances. These notes, both prior to and on smoking in the main stream and sidestream may now be readily controlled and maintained at the desired uniform level regardless of variations in the tobacco components of the blend; or the nature of the filter used in conjunction with the tobacco article.

This invention further provides improved tobacco additives and additives for materials used in the fabrication of tobacco articles and methods whereby desirable sweet, hay-like, Virginia tobacco-like, flue cured-like aromas with floral and sweet hay nuances may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the hydroxy cyclohexenone derivatives of our invention.

In addition to the hydroxy cyclohexenone derivatives of our invention, other flavoring and aroma additives may be added to the smoking tobacco material or substitute therefor either separately or in mixture with one or more of the hydroxy cyclohexenone derivatives:

I. Synthetic Materials

Beta-methyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1,2-methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2,1-b)-furan;
4-Hydroxy hexanoic acid, gamma lactone;
Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil;
Origanum oil.

An aroma and flavoring concentrate containing one or more of the hydroxy cyclohexenone derivatives of our invention and, if desired, one or more of the above indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of sweet, hay-like, Virginia tobacco-like, flue cured-like aromas with floral and sweet hay nuances, we have found that satisfactory results are obtained if the proportion by weight of the sum total of the hydroxy cyclohexenone derivatives to smoking tobacco material is between 50 ppm and 500 ppm (.005%-.05%) of the active ingredients to the smoking tobacco material. We have further found that satisfactory results are obtained if the proportion by weight of the sum total of the hydroxy cyclohexenone derivatives used to flavoring material is between 0.05:1 and 0.50:1.

Any convenient method for incorporating the hydroxy cyclohexenone derivatives in the tobacco product may be employed. Thus, the hydroxy cyclohexenone derivatives taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material or filter may be dipped into such solution. Under certain circumstances, a solution of hydroxy cyclohexenone derivatives taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more hydroxy cyclohexenone derivatives of our our invention in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of 4-butyl-4-hydroxy-3,5,5-trimethyl-2-cyclohexen-1-one of our invention, in an amount to provide a tobacco composition containing 800 ppm by weight of 4-butyl-4-hydroxy-3,5,5-trimethyl-2-cyclohexen-1-one on a dry basis. Thereafter, the alcohol is removed by evaporation and the tobacco is manufactured into cigarettes by the usual techniques. The cigarette when treated as indicated has a desired and pleasing sweet, hay-like, Virginia flue cured tobacco-like aroma with floral and moss-like nuances detectable in the main and side streams when the cigarette is smoked.

While our invention is particularly useful in the manufacture of smoking tobacco, such as cigarette tobacco, cigar tobacco, and pipe tobacco, other tobacco products formed from sheeted tobacco dust or fines may also be used. As stated supra, the hydroxy cyclohexenone derivatives of our invention can be incorporated with materials such as filter tip materials, seam paste, packaging materials and the like which are used along with the tobacco to form a product adapted for smoking. Furthermore, the hydroxy cyclohexenone derivatives of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

The following examples are given to illustrate embodiments of the invention as it is presently preferred to practice it. It will be understood that these examples are illustrative, and the invention is not to be considered as restricted thereto except as indicated in the appended claims. All parts and percentages are by weight unless otherwise indicated.

EXAMPLE I

PREPARATION OF 1,3,5,5-TETRAMETHYLCYCLOHEXA-1,3-DIENE

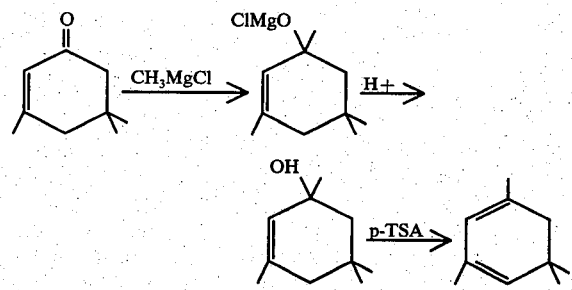

To a 5 liter flask fitted with a stirrer, thermometer, dropping funnel, reflux condenser, drying tube and nitrogen purge is charged 2100 ml (6.3 moles) of a 3 m solution of methyl magnesium chloride in tetrahydrofuran. The flask and contents are cooled to 0° C and 730 g (5.3 moles) of isophorone is added at 0°-5° C over a two hour period. The mixture is allowed to warm to room temperature and to stand overnight. The reaction mixture is poured over a mixture of 2800 g of ice and 370 g of glacial acetic acid. When all the ice melts, the layers are separated and the organics are washed twice with 500 ml of water. The solvent is removed on a rotary evaporator and the product is transferred to a 2 liter flask fitted with a condenser and a water separator. Benzene (300 ml) and p-toluenesulfonic acid (0.5 g) are added and the mixture is refluxed until no additional water separated. The product is distilled on a 12 inch Goodloe column using a reflux ratio of 9:1. A total of 494 g of product is obtained (b.p. 66°-67° C at 42 mm Hg) which is predominantly 1,3,5,5,-tetramethylcyclohexa-1,3-diene.

EXAMPLE II

PREPARATION OF 4-HYDROXY-2,4,6,6-TETRAMETHYLCYCLOHEX-2-EN-1-ONE AND 2,4,4,6-TETRAMETHYLCYCLOHEXA-2,5-DIENE-1-ONE

Reaction:

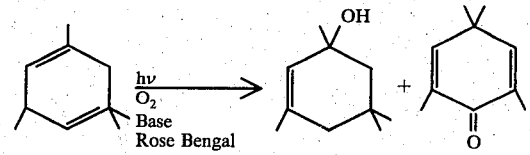

A solution of 40 g (0.3 moles) of 1,3,5,5-tetramethylcyclohexa-1,3-diene (prepared as in Example I), 13 g (0.23 moles) of potassium hydroxide and 0.3 g of Rose Bengal in 600 ml of methanol is placed in a flask and irradiated with a 450 watt tungsten photo lamp over a period of two hours. A steady stream of oxygen is bubbled through the solution during irradiation. At the end of the two hour irradiation period analysis of a sample of the reaction mixture by GLC (10 feet × ⅛ inch 10% Carbowax 20M on Chromasorb W, programmed from 80°-220° C at 8°/min.) shows that the starting material is completely consumed and two products had formed. Both products are trapped from the GLC column and analyzed. The first (about 20% of the reaction product) is found to be 2,4,4,6-tetramethylcyclohexa-2,5-diene-1-one (compound A) and exhibits the following spectral properties:

| NMR (δ) ppm | Interpretation |
|---|---|
| 1.2 | (s, 6H) |
| 1.9 | (s, 6H) |
| 6.58 | (s, 2H) |

Infrared spectrum:
1630 cm$^{-1}$ (C=O)
Mass Spectral analysis (m/e):
107, 150 (m), 135, 39, 41, 91.

Figure 2:
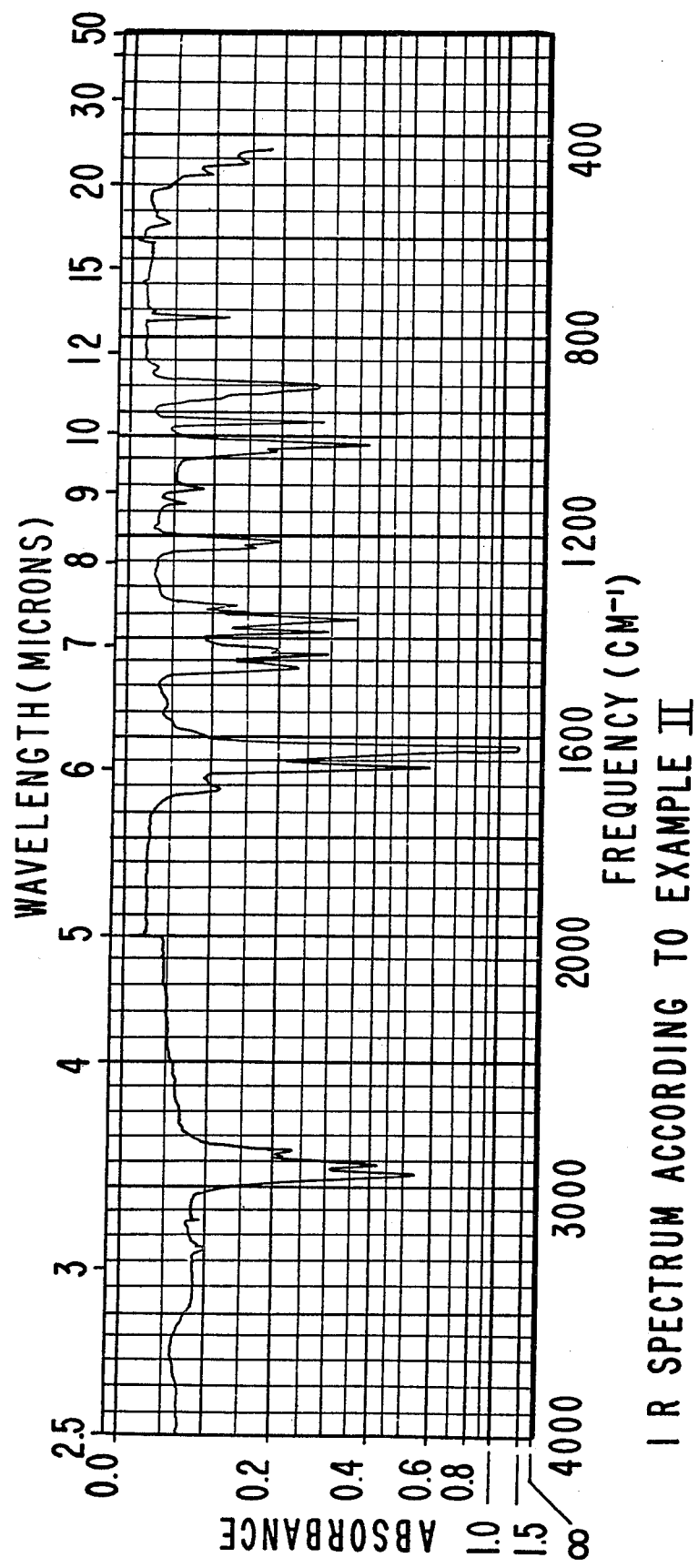
FIG. 2 represents the Infrared spectrum for one of the compounds produced according to Example II, namely, 4-hydroxy-2,4,6,6-tetramethylcyclohex-2-en-1-one and 2,4,4,6-tetramethylcyclohexa-2,5-diene-1-one.

The NMR spectrum is set forth in FIG. 1. The Infrared spectrum is set forth in FIG. 2.

The second (about 80% of the product mixture) is found to be 4-hydroxy-2,4,6,6-tetramethylcyclohex-2- en-1-one (compound B) and exhibits the following spectral properties:

| NMR (δ) ppm | Interpretation |
|---|---|
| 1.16 | (s, 3H) |
| 1.28 | (s, 3H) |
| 1.44 | (s, 3H) |
| 1.81 | (d, 3H) |
| 2.02 | (s, 2H) |
| 6.41 | (d, 1H) |

Infrared spectrum:
1630 cm$^{-1}$ (C=O)
Mass Spectral analysis (m/e):
112, 69, 43, 39, 41, 84

Figure 3:
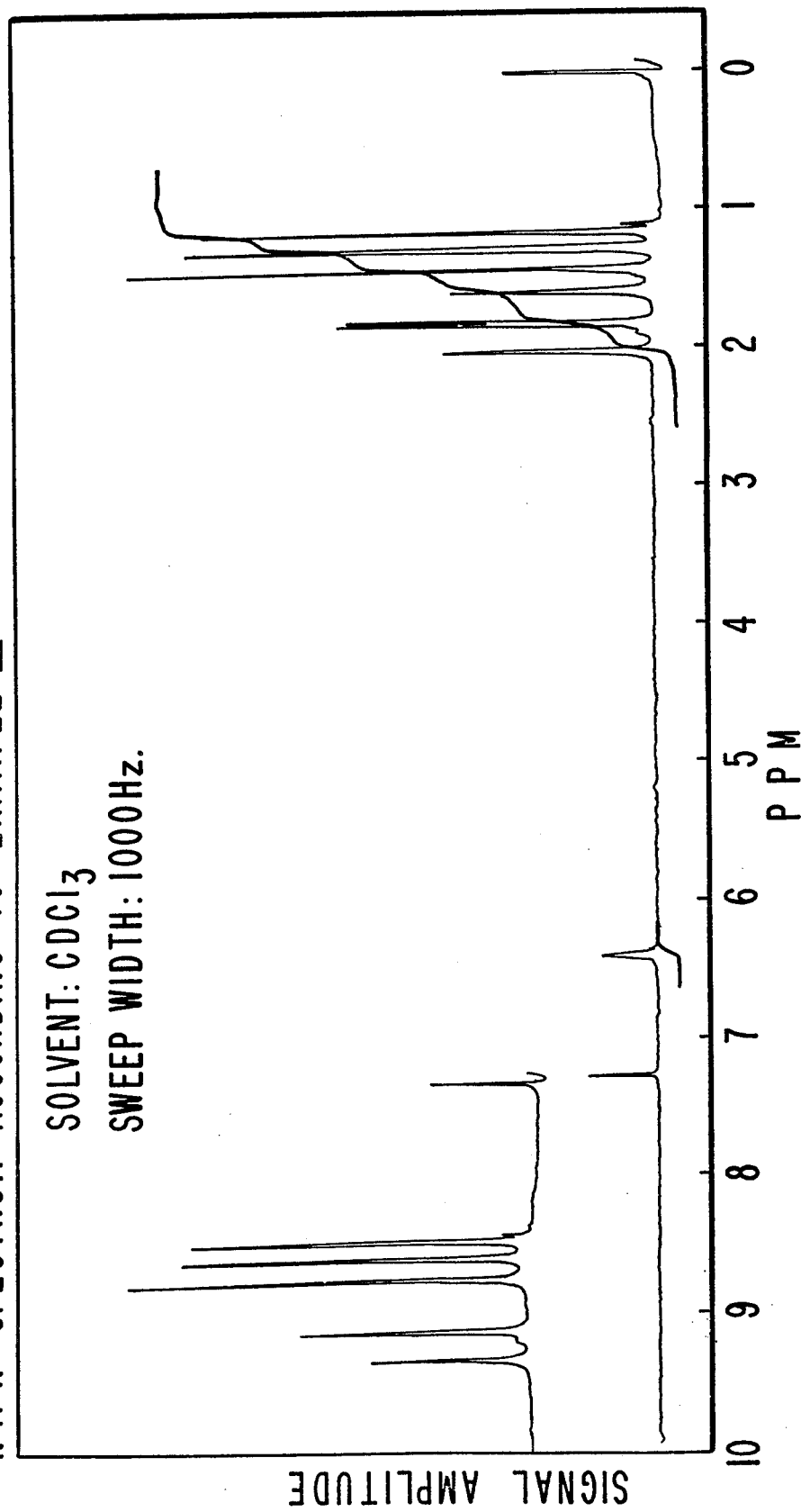
FIG. 3 represents the NMR spectrum for one of the compounds produced according to Example II, 4-hydroxy-2,4,6,6-tetramethylcyclohex-2-en-1-one.
Figure 4:
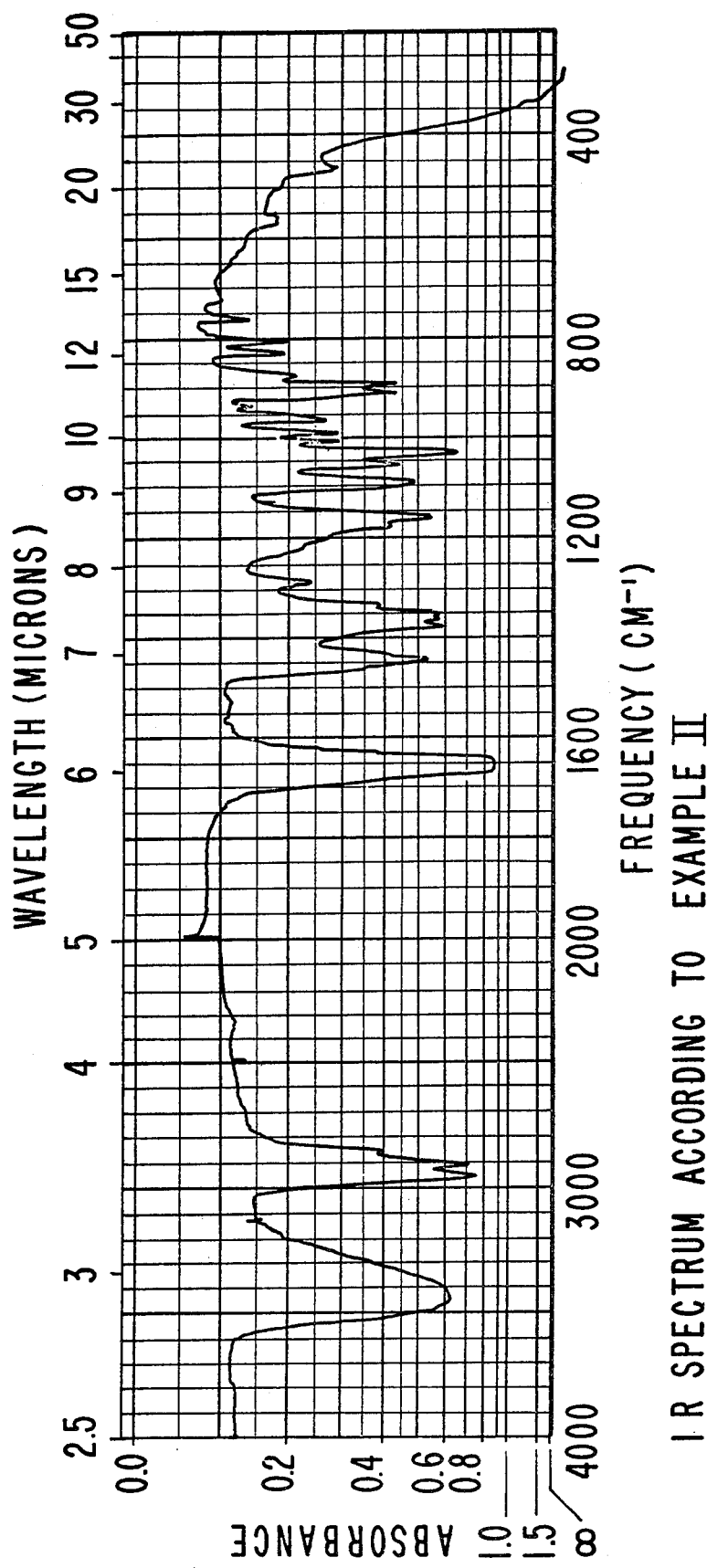
FIG. 4 represents the Infrared spectrum for one of the compounds produced according to Example II, 4-hydroxy-2,4,6,6-tetramethylcyclohex-2-en-1-one.

The NMR spectrum is set forth in FIG. 3. The Infrared spectrum is set forth in FIG. 4.

The reaction mixture is poured into 500 of water and the organics are extracted with four 100 ml portions of ether. The ether is removed by means of a rotary evaporator and the two products are separated by means of a careful distillation. Compound A is obtained first and has a b.p. of 60° C at 1.5 mm. Compound B distills second with a b.p. of 100° C at 1.5 mm.

EXAMPLE III

PREPARATION OF 2,7,9,9-TETRAMETHYL-1,4-DIOXASPIRO[4,5]-DEC-6-EN-8-ONE

Reaction:

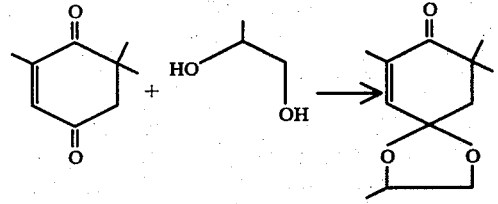

To a 2 liter flask fitted with a reflux condenser, a water separator and a stirrer is charged 265 g of 2,6,6-trimethylcyclohex-2-en-1,4-dione (prepared by the method described in Helv.Chim.Acta. 39, 2041(1956)), 266 g of propylene glycol, 500 ml of benzene and 1 g of p-toluenesulfonic acid. The reactants are stirred and refluxed until no additional water is collected in the water separator. The product is washed with water to a pH of 6 and the solvent is stripped off. The residue is vacuum distilled through a 9 inch Goodloe column to yield 257 g of product, b.p. 92° at 1 mm Hg (80% yield).

EXAMPLE IV

PREPARATION OF 4-BUTYL-4-HYDROXY-3,5,5-TRIMETHYL-2-CYCLOHEXEN-1-ONE

Reaction:

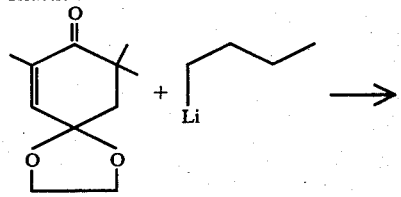

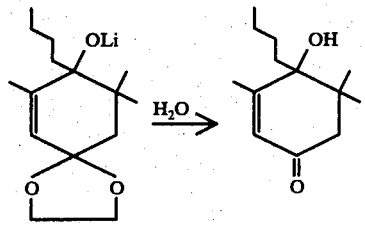

A solution of 20 g of 2,7,9,9-tetramethyl-1,4-dioxaspiro-[4,5]dec-6-en-8-one (prepared by the method of Example III) in hexane is stirred while a solution of n-butyl lithium in hexane is added dropwise. When no additional exotherm occurred the addition is stopped and the mixture is stirred for about 15 minutes. Water is added with stirring to hydrolyze the lithium salt. The organic layer is separated and the hexane is allowed to evaporate, leaving oily crystals which are recrystallized from cyclohexane yielding 10 g of 4-butyl-4-hydroxy-3,5,5-trimethyl-2-cyclohexen-1-one, m.p. 90°–93° C. The compound exhibits the following spectral characteristics:

| NMR (δ) ppm | Interpretation |
|---|---|
| 0.87 | (t, 3H) |
| 1.02 | (s, 3H) |
| 1.05 | (s, 3H) |
| 1.05–2.1 | (complex signals, 4H) |
| 1.98 | (s, 3H) |
| 2.35 | (q, 4H) |

Infrared analysis:
1640 cm$^{-1}$ (C=O)
Mass Spectral analysis (m/e):
43, 41, 29, 39, 27, 28, 111, 154, 210 (m).

Figure 5:
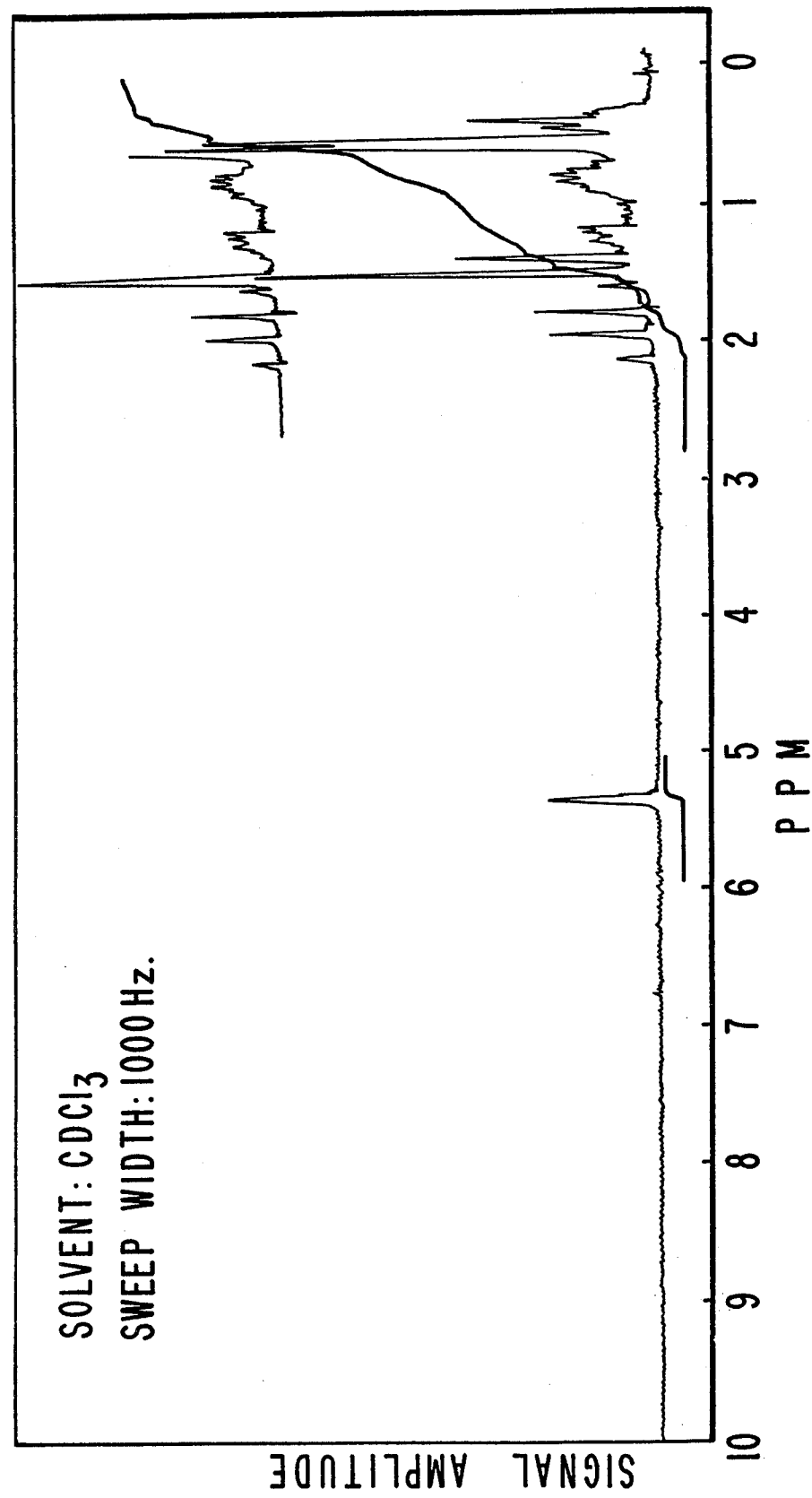
FIG. 5 represents the NMR spectrum for the compound prepared according to Example IV, 4-butyl-4-hydroxy-3,5,5-trimethyl-2-cyclohexen-1-one.
Figure 6:
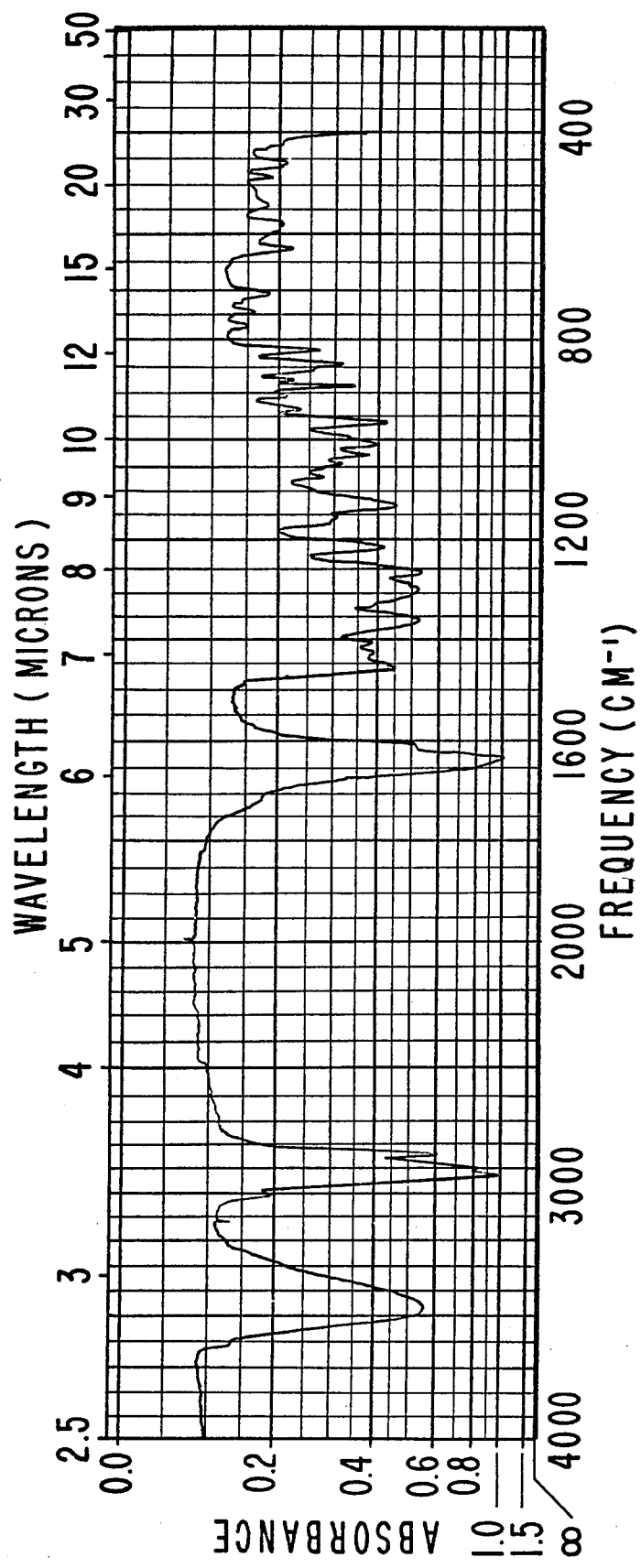
FIG. 6 represents the Infrared spectrum for the compound prepared according to Example IV, 4-butyl-4-hydroxy-3,5,5-trimethyl-2-cyclohexen-1-one.

The NMR spectrum is set forth in FIG. 5. The Infrared spectrum is set forth in FIG. 6.

EXAMPLE V

GERANIUM PERFUME FORMULATION

The following mixture is prepared:

| Ingredients | Parts by Weight |
|---|---|
| Geraniol Coeur | 100.0 |
| Citronellol Coeur | 130.0 |
| Linalool | 5.0 |
| Citronellyl Formate | 25.0 |
| Geranyl Acetate | 10.0 |
| Benzyl | 2.0 |
| Guaicwood | 10.0 |
| 4-Hydroxy-2,4,6,6-tetramethylcyclohex-2-en-1-one, produced according to Example II | 30.0 |

The 4-hydroxy-2,4,6,6-tetramethylcyclohex-2-en-1-one imparts the green, minty, herbaceous tone of geranium to this synthetic geranium formulation.

EXAMPLE VI

PREPARATION OF SOAP COMPOSITION

One hundred grams of soap chips are mixed with one gram of the perfume composition of Example V until a substantially homogeneous composition is obtained. The perfumed soap composition exhibits a green, minty, herbaceous note so essential to geranium.

EXAMPLE VII

PREPARATION OF A DETERGENT COMPOSITION

A total of 100 grams of a detergent powder (Lysine salt of n-dodecylbenzenesulfonic acid, as more specifically described in U.S. Pat. No. 3,948,818, issued on Apr. 6, 1976) is mixed with 0.15 grams of the perfume composition of Example V until a substantially homogeneous composition is prepared. This composition exhibits a green, minty, herbaceous note so essential to geranium.

EXAMPLE VIII

PREPARATION OF A COSMETIC POWDER COMPOSITION

A cosmetic powder is prepared by mixing in a ball mill, 100 grams of talcum powder with 2 grams of the composition of Example V. It has a green, minty, herbaceous note so essential to geranium.

EXAMPLE IX

PERFUMED LIQUID DETERGENT

Concentrated liquid detergent (Lysine salt of n-dodecylbenzenesulfonic acid, as more specifically described in U.S. Pat. No. 3,948,818, issued on Apr. 6, 1976) with a geranium character is obtained containing 1.0%, 1.5% and 2.0% of the composition of Example V. It is prepared by adding and homogeneously mixing the appropriate quantity of the composition of Example V in the liquid detergent. The detergents all possess a geranium aroma with green, minty and herbaceous notes, the intensity increasing with greater concentrations of the composition of Example V.

EXAMPLE X

COLOGNE

The composition of Example V is incorporated in a cologne at a concentration of 2.5% in 85% aqueous ethanol; and into a handkerchief perfume at a concentration of 20% (in 95% aqueous ethanol). A distinct and definite geranium fragrance containing green, minty and herbaceous notes essential to geranium is imparted to the cologne and to the handkerchief perfume.

EXAMPLE XI

PREPARATION OF A COSMETIC POWDER COMPOSITION

A cosmetic powder is prepared by mixing in a ball mill, 100 g of talcum powder with 0.25 g of 4-hydroxy-2,4,6,6-tetramethylcyclohex-2-en-1-one prepared according to Example II. It has an excellent green, minty and herbaceous aroma.

EXAMPLE XII

PERFUMED LIQUID DETERGENT

Concentrated liquid detergents (Lysine salt of n-dodecylbenzenesulfonic acid, as more specifically described in U.S. Pat. No. 3,948,818, issued on Apr. 6, 1976) with a green, minty and herbaceous aroma are prepared containing 0.10%, 0.15% and 0.20% of 4-hydroxy-2,4,6,6-tetramethylcyclohex-2-en-1-one prepared according to Example II. They are prepared by adding and homogeneously mixing the appropriate quantity of 4-hydroxy-2,4,6,6-tetramethylcyclohex-2-en-1-one in the liquid detergent. The detergents all possess a green, minty and herbaceous aroma, the intensity increasing with greater concentrations of 4-hydroxy-2,4,6,6-tetramethylcyclohex-2-en-1-one.

EXAMPLE XIII

PREPARATION OF A COLOGNE AND HANDKERCHIEF PERFUME

4-Hydroxy-2,4,6,6-tetramethylcyclohex-2-en-1-one prepared according to the process of Example II is incorporated in a cologne at a concentration of 2.5% in 85% aqueous ethanol; and into a handkerchief perfume at a concentration of 20% (in 95% aqueous ethanol). A distinct and definite green, minty and herbaceous aroma is imparted to the cologne and to the handkerchief perfume.

EXAMPLE XIV

PREPARATION OF SOAP COMPOSITION

One hundred grams of soap chips are mixed with one gram of 4-hydroxy-2,4,6,6-tetramethylcyclohex-2-en-1-one of Example II until a substantially homogeneous composition is obtained. The perfumed soap composition manifests an excellent green, minty and herbaceous aroma.

EXAMPLE XV

PREPARATION OF A DETERGENT COMPOSITION

A total of 100 g of a detergent powder (Lysine salt of n-dodecylbenzenesulfonic acid, as more specifically described in U.S. Pat. No. 3,948,818, issued on Apr. 6, 1976) is mixed with 0.15 g of the 4-hydroxy-2,4,6,6-tetramethylcyclohex-2-en-1-one of Example II until a substantially homogeneous composition is obtained. This composition has an excellent green, minty and herbaceous aroma.

EXAMPLE XVI

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes.

| Ingredient | Parts by Weight |
|---|---|
| Ethyl Butyrate | .05 |
| Ethyl valerate | .05 |
| Maltol | 2.00 |
| Cocoa Extract | 26.00 |
| Coffee Extract | 10.00 |
| Ethyl Alcohol | 20.00 |
| Water | 41.90 |

The above flavor is incorporated into model "filter" cigarettes at the rate of 0.1%. One-third of these model cigarettes are treated in the tobacco section with the 4-hydroxy-2,4,6,6-tetramethylcyclohex-2-en-1-one produced according to Example II at 200 ppm per cigarette. Another third of these model cigarettes are treated in the filter with the 4-hydroxy-2,4,6,6-tetramethylcyclohex-2-en-1-one at the rate of $2 \times 10^{-5}$ gm. and $3 \times 10^{-5}$ gm. When evaluated by paired comparison, the cigarettes treated both in the tobacco and in the filter with the 4-hydroxy-2,4,6,6-tetramethylcyclohex-2-en-1-one are found, in smoke flavor, to be more aromatic, sweeter, cooling (sensation in the mouth) and containing sweet tobacco-like, floral and green nuances.

EXAMPLE XVII

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes:

| Ingredient | Parts by Weight |
|---|---|
| Ethyl Butyrate | .05 |
| Ethyl valerate | .05 |
| Maltol | 2.00 |
| Cocoa Extract | 26.00 |
| Coffee Extract | 10.00 |
| Ethyl Alcohol | 20.00 |
| Water | 41.90 |

The above flavor is incorporated into model "filter" cigarettes at the rate of 0.1%. One-third of these model cigarettes are treated in the tobacco section with the 4-butyl-4-hydroxy-3,5,5-trimethyl-2-cyclohexen-1-one produced according to Example IV at 200 ppm per cigarette. Another third of these model cigarettes are treated in the filter with the 4-butyl-4-hydroxy-3,5,5-trimethyl-2-cyclohexen-1-one at the rate of $2 \times 10^{-5}$ gm. and $3 \times 10^{-5}$ gm. When evaluated by paired comparison the cigarettes treated both in the tobacco and in the filter with the 4-butyl-4-hydroxy-3,5,5-trimethyl-2-cyclohexen-1-one are found in smoke flavor to have sweet hay notes, tobacco-like notes and Virginia flue cured-like notes; and are also found to be more aromatic and Virginia tobacco-like.

EXAMPLE XVIII

RASPBERRY FLAVOR FORMULATION

The following formulation is prepared:

| Ingredient | Parts by Weight |
|---|---|
| Raspberry ketone (oxyphenylon) | 4 |
| Vanillin | 1 |
| Maltol | 2 |
| Alpha-ionone | 0.5 |
| Isobutylacetate | 20 |
| Ethylbutyrate | 5.5 |
| Dimethyl sulfide | 1 |
| Acetic acid | 30 |
| Acetaldehyde | 16 |
| Propylene glycol | 920 |

When added at the rate of 1% to the above formulation the 4-hydroxy-2,4,6,6-tetramethylcyclohex-2-en-1-one adds a more natural character thereto. A 5-member bench panel unanimously agrees that the formulation containing 1% of 4-hydroxy-2,4,6,6-tetramethylcyclohex-2-en-1-one is more raspberry-kernel like; more piney; has a wild raspberry or herbaceous taste and has a natural berry character. The flavor formulation containing the 1% of 4-hydroxy-2,4,6,6-tetramethylcyclohex-2-en-1-one is unanimously preferred over the flavor formulation not containing any 4-hydroxy-2,4,6,6-tetramethylcyclohex-2-en-1-one. The flavor formulations are compared side-by-side at the rate of 40 ppm in water.

EXAMPLE XIX

The following mixture is prepared:

| Ingredients | Parts by Weight |
|---|---|
| Natural Raspberry Concentrate Juice | 2 1/2% |
| Water | 85% |
| Sugar syrup, (37.5° Baume) | 12 1/2% |

The wild raspberry, herbaceous and seedy, raspberry kernel notes of this raspberry juice is imparted in increased strength by addition of 4-hydroxy-2,4,6,6-tetramethylcyclohex-2-en-1-one at the rate of from 20 parts per million up to 50 parts per million.

EXAMPLE XX

To the raspberry formulation of Example XVIII, 4-hydroxy-2,4,6,6-tetramethylcyclohex-2-en-1-one at the rate of 0.2% is added. This material is then called the "test composition". The raspberry formulation without 4-hydroxy-2,4,6,6-tetramethylcyclohex-2-en-1-one is called the "control composition".

The test and control compositions are added to the food products described hereinafter in the proportions shown for 10 kilograms of material to be flavored:

| Pudding | 5–10 grams (0.15–.1%) |
|---|---|
| Cooked sugar | 15–20 grams (.15–2%) |

Cooked sugar — 100 ml of sugar syrup (prepared by dissolving 1 kilogram of sucrose in 600 ml of water) and 20 grams of glucose are mixed together and slowly heated to 145° C. The flavor is added and the mass allowed to cool and harden.

Pudding — To 500 ml of warmed milk are added with stirring a mixture of 60 grams sucrose and 3 grams of pectin. The mixture is boiled for a few seconds and the flavor is added. The mixture was allowed to cool.

The finished foodstuff samples are tested by a panel of trained persons who express their views about the flavor of the samples. All members of the panel prefer the test samples having a more distinguished wild raspberry aroma with taste of the wild raspberries and its herbaceous and kernel notes.

What is claimed is:

1. A process for augmenting or enhancing the organoleptic properties of a foodstuff by adding to said foodstuff from 0.5 parts per million up to about 100 parts per million based on the total composition of 4-hydroxy-2,4,6,6-tetramethylcyclohex-2-en-1-one.

2. A flavor modifying composition comprising about 0.1% up to about 15% by weight based on the total weight of the composition of 4-hydroxy-2,4,6,6-tetramethylcyclohex-2-en-1-one and as a flavor adjuvant a compound selected from the group consisting of p-hydroxybenzyl acetone, maltol, benzyl acetate, methyl cinnamate, geraniol, ethyl methyl phenyl glycidate, vanillin, methyl anthranilate, alpha-ionone, gamma undecalactone, ethyl pelargonate, isoamyl acetate, acetaldehyde, dimethyl sulfide, isobutyl acetate, acetic acid, ethyl butyrate, diacetyl, anethole, cis-3-hexenol-1, naphthyl ethyl ether, ethyl acetate, isoamyl butyrate, 2-methyl-2-pentenoic acid, 2-(4-hydroxy-4-methylpentyl)-norbornadiene, 4-allyl-1,2,6-trimethoxybenzene, cassia oil, eugenol, caryophyllene, guiacol, cinnamaldehyde, 5-methylfurfural, cuminaldehyde, cinnamyl formate, methyl cinnamate, furfural, 2,3-dimethylpyrazine, 2-ethyl-3-methylpyrazine, 3-phenyl-4-pentenal, 2-phenyl-2-hexenal, 2-phenyl-2-pentenal, 3-phenyl-4-pentenal diethyl acetal, 1-crotonyl-2,2,6-trimethylcyclohex-1-ene, 1-crotonyl-2,2,6-trimethylcyclohexa-1,5-diene, 2,2,6-trimethylcyclohex-1-ene carboxaldehyde and 4-propenyl-1,2,6-trimethoxybenzene.

* * * * *